(12) United States Patent
Owen (10) Patent No.: US 7,107,851 B2
(45) Date of Patent: Sep. 19, 2006

(54) PROCESSING DATA, FOR IMPROVED, ACCURACY, FROM DEVICE FOR MEASURING SPEED OF SOUND IN A GAS

(75) Inventor: Thomas E. Owen, Helotes, TX (US)

(73) Assignee: Southwest Research Institute, San Antonio, TX (US)

(\*) Notice: Subject to any disclaimer, the term of this patent is extended or adjusted under 35 U.S.C. 154(b) by 204 days.

(21) Appl. No.: 10/894,084

(22) Filed: Jul. 19, 2004

(65) Prior Publication Data

US 2005/0028579 A1 Feb. 10, 2005

Related U.S. Application Data

(63) Continuation of application No. 10/406,518, filed on Apr. 3, 2003, now Pat. No. 6,823,716
(60) Provisional application No. 60/427,099, filed on Nov. 18, 2002.

(51) Int. Cl.
*G01N 29/02* (2006.01)

(52) U.S. Cl. .............. 73/597; 73/602; 702/54
(58) Field of Classification Search .......... 73/579, 73/597, 598, 599, 627, 1.82, 1.86, 602, 24.01, 73/24.06; 702/54
See application file for complete search history.

(56) References Cited

U.S. PATENT DOCUMENTS

| | | | | |
|---|---|---|---|---|
| 3,949,605 A | * | 4/1976 | Stallworth et al. | 73/861.27 |
| 4,567,770 A | | 2/1986 | Rumbold et al. | 73/644 |
| 4,571,693 A | | 2/1986 | Birchak et al. | 364/509 |
| 4,909,080 A | | 3/1990 | Kikuta et al. | 73/290 V |
| 4,938,066 A | | 7/1990 | Dorr | 73/597 |
| 4,991,976 A | | 2/1991 | Byles | 374/135 |
| 5,461,931 A | | 10/1995 | Gill | 73/861.28 |
| 5,526,699 A | | 6/1996 | Dorr | 73/861.28 |
| 5,581,014 A | | 12/1996 | Douglas | 73/24.01 |
| 5,697,346 A | * | 12/1997 | Beck | 123/494 |
| 2003/0114992 A1 | * | 6/2003 | Morrow et al. | 702/23 |

FOREIGN PATENT DOCUMENTS

| | | | |
|---|---|---|---|
| JP | 56002567 A | * | 1/1981 |
| JP | 2001255313 A | * | 9/2001 |
| WO | 99/67649 | | 12/1999 |
| WO | 02/44662 | | 6/2002 |

OTHER PUBLICATIONS

International Search Report for PCT/US 03/36034, 5 pages, Mailed Oct. 5, 2004.

* cited by examiner

*Primary Examiner*—John E. Chapman
*Assistant Examiner*—Rose M. Miller
(74) *Attorney, Agent, or Firm*—Baker Botts L.L.P.

(57) ABSTRACT

A method, used in connection with a pulse-echo type sensor for determining the speed of sound in a gas, for improving the accuracy of speed of sound measurements. The sensor operates on the principle that speed of sound can be derived from the difference between the two-way travel time of signals reflected from two different target faces of the sensor. This time difference is derived by computing the cross correlation between the two reflections. The cross correlation function may be fitted to a parabola whose vertex represents the optimum time coordinate of the coherence peak, thereby providing an accurate measure of the two-way time diffference.

27 Claims, 9 Drawing Sheets

(4 of 9 Drawing Sheet(s) Filed in Color)

PROCESSING DATA, FOR IMPROVED, ACCURACY, FROM DEVICE FOR MEASURING SPEED OF SOUND IN A GAS

RELATED PATENT APPLICATION

This application is a continuation-in-part of U.S. patent application Ser. No. 10/406,518, filed Apr. 3, 2003, and entitled "Device for Precision Measurement of Speed of Sound in a Gas" now U.S. Pat. No. 6,823,716, which claims priority to U.S. Provisional Application No. 60/427,099 filed Nov. 18, 2002 and entitled Device for Precision Measurement of Speed of Sound in a Gas.

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to the field of ultrasonic measurements, and more particularly, to processing data from a device for measuring the speed of sound in a gas using transit time of an ultrasonic pulse.

Background of the Invention

A unique physical characteristc of any gas is the speed of sound through that gas at specified pressure and temperature conditions. This characteristic, in combination with the temperature and pressure of the gas, may be used as a direct testing method for identifying individual pure gases, and may serve as one of several measurable physical parameters by which certain gas mixtures containing two or more known gas constituents may be quantitatively analyzed in terms of their concentrations.

The natural gas industry speed of sound measurement is gases are important because the speed of sound, in combination with the gas temperature, pressure, and the amount of non-hydrocarbon diluent gases, may be used to experimentally characterize the gas and infer the heating value energy content of the gas. This method of determining the energy content of natural gas does not require any additional information or measurement defining the hydrocarbon constituents or their concentrations. This inferential method of determining gas heating value is described in U.S patent Nos. 6,604,051 and 6,704,660, assigned to Southwest Research Institute.

The inferential gas energy measurement method has been extended to a "two state" method, which is used to inferentially determine both the heating value and the nitrogen dilution concentration of gas mixtures given experimental measurements of gas pressure, temperature, speed of sound, and carbon dioxide concentration. This "two-state" method is described in U.S. patent No. 6,804,610, entitled "Indirect Measurement of Nitrogen in a Multi-Component Gas by Measuring the Speed of Sound at Two States of the Gas", assigned to Southwest Research Institute. Parametric studies of the two-state inferential algorithm based on 86 different natural gas mixtures having sound speeds in the ragne of about 1,300–1, 500 ft/sec indicate that the speed of sound must be accurate to within ±0.1 ft/sec or less in the gas pressure range of 50–200 psia in order to provide suitably accurate output values of gas heating value and nitrogen concentration. This degree of accuracy requires that the speed of sound sensor provide measured and resolved values of the gas speed of sound to within about ±70 parts per million at two arbitrary but accurately measured pressure-temperature states. Obtaining an accurate inferential estimate of nitrogen, which cannot be sensed directly by other practical means, imposes this relatively high precision in speed of sound in in comparison with inferential estimates of gas heating value obtained with a simpler algorithm when the nitrogen concentration is known in advance from gas chromatography measurements.

Achieving the needed accuracy in the measured speed of sound requires a precision experimental speed of sound sensing technique and a dedicated computational capability for numerically processing and analyzing the sensor output data.

BRIEF DESCRIPTION OF THE FIGURES

The file of this patent contains at least one drawing executed in color. Copies of this patent with color drawings will be provided by the Patent and Trademark Office upon request and payment of the necessary fee.

DETAILED DESCRIPTION OF THE INVENTION

Overview of Two-Reflector Pulse Echo Speed of Sound Sensors and Sensor Data Processing One approach to measuring the speed of sound in gas involves measurement of the transit time of an ultrasonic pulse traveling over a known propagation distance in the gas. This technique typically employs one or more piezoelectric transducers to generate and detect sound waves in the frequency range of about 20 kHz to 1 MHz and higher. A particular technique known as a "pulse echo" technique uses a single transducer as both the transmitter and the receiver. The generated sound wave is reflected back to the source transducer from a target located at a known distance from the transducer, and is received by the same transducer. If the distance between the transducer and the reflecting target is D, and the measured two-way travel time is t, then the speed of sound is represented by:

$$v_{gas} = 2D/t. \quad (1)$$

This method is advantageous because it uses only one transducer. However, in applications requiring high-precision speed of sound measurements, the method has the disadvantage of introducing time delay errors.

To reduce the time delay error, the pulse echo method may be modified to measure a time difference between two received signals. A transmitted wave is reflected from two different targets rather than a single target. The distance, d, between the two targets is known. Using this method, the speed of sound is represented by:

$$v_{gas} = 2d/\Delta t, \quad (2)$$

where $\Delta t$ is the time difference between the two received signals.

With this two-reflector method, the two ultrasonic wave pulses returning to the transducer will be similar in amplitude and in waveform so that they may be accurately compared and their relative two-way travel time delay, $\Delta t$, measured. In particular, a method of cross correlation analysis may be used as the means for accurately comparing the two reflected pulses in a statistical sense and, in so doing, determine with good accuracy their relative time delay.

Figure 1:
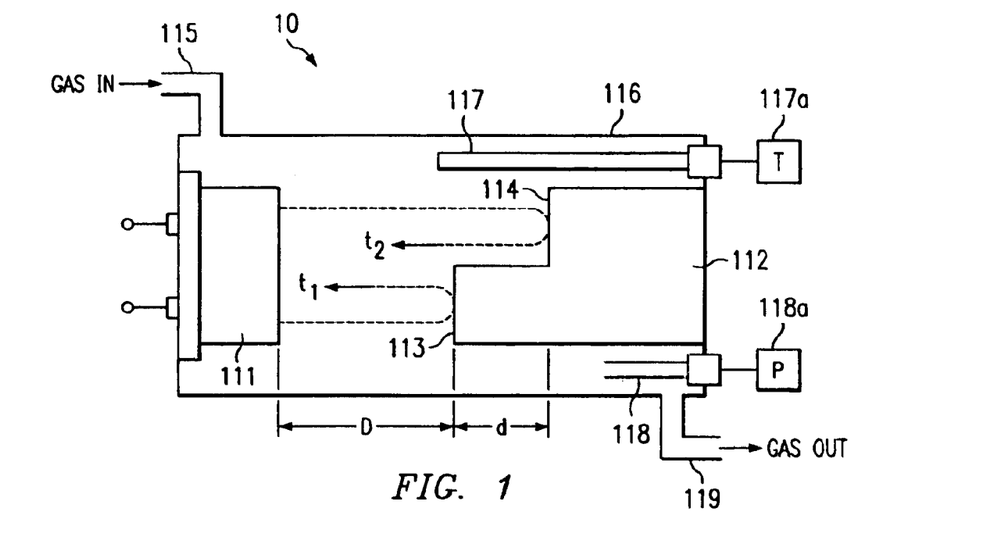
FIG. 1 shows the basic arrangement of the speed of sound sensor using the two-reflector technique in accordance with the invention.

FIG. 1 illustrates an example of a two-reflector transit time speed of sound sensor 10. The main components of sensor 10 are the speed of sound chamber 116, the ultrasonic transmit-receive transducer 111, and the two-reflector target block 112. In general, sensor and the transducer 111 and target block 112, comprising the primary components of sensor 10, are cylindrical in shape, having a common axis of assembly.

Figure 2:
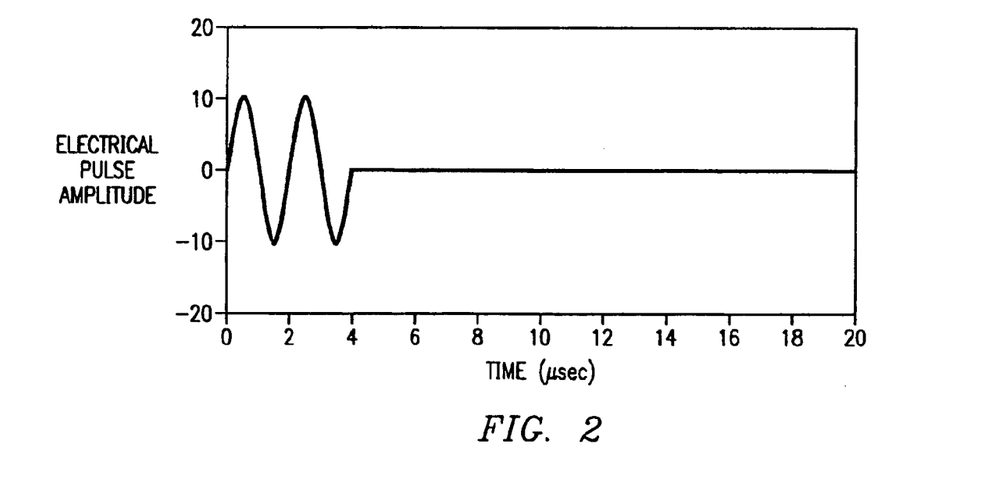
FIG. 2 shows a typical electrical excitation voltage pulse applied to the ultrasonic transducer.
Figure 3:
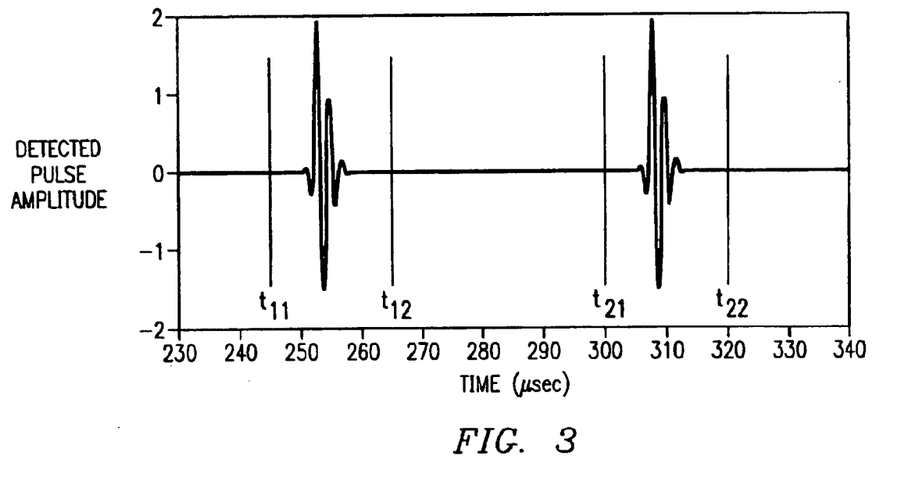
FIG. 3 shows the two ultrasonic pulses reflected from the dual-face target.

FIG. 2 illustrates a typical excitation voltage waveform applied to the transmit-receive transducer 111 to produce the transmitted ultrasonic pulse in the gas. FIG. 3 illustrates the two ultrasonic pulses after propagating to and reflecting from the target block 112 and being detected by the transmit-receive transducer 111.

In operation, as further explained below, sensor 10 is capable of yielding precision measurements of the speed of sound in gas and vapor mixtures such as those comprising natural gas. It accepts a flowing stream of gas at gas inlet 115 previously brought to thermal equilibrium with the temperature of the test chamber 116, and measures the gas temperature by means of temperature sensor 117 located within chamber 16 and temperature transmitter 117a and the gas pressure by means of pressure sensor 118 in direct fluid communication with chamber 116 and pressure transmitter 118a, and provides for exit of the gas at gas outlet 119. The transmit-receive transducer 111 is mounted at one end of the cylindrical test chamber 116 with its active face exposed to the gas contained within the chamber 116. The electrical leads of transducer 111 are brought out of the chamber 116 via pressure-sealed electrical feedthrough terminals to maintain the pressure integrity of the chamber 116. The reflector target block 112 is made from one piece of material to provide two planar semicircular reflecting surfaces 113 and 114 accurately separated by a distance, d, along the axial length of test chamber 116 and oriented parallel to the face of transducer 111 located at a spacing, D, away from reflecting surface 113 along the axial length of the test chamber 116.

The two-reflector target 116 is made from a single target piece comprised of a material having a very low coefficient of thermal expansion. Specifically, the reflecting surfaces of the two-reflector target 116 may be made to be physically identical in all respects and made of a material such as Invar© so as to have negligible thermal expansion effects. The relative time delay between the two reflections will then be governed by the distance, 2d, which may be very accurately measured and known.

Sensor 10 is operated in the test gas by first applying an electrical excitation pulse signal to the terminals of transducer 111 causing its piezoelectric transducer element to generate a sound wave pulse in the gas. The electrical excitation pulse is typically a sinusoidal signal having a finite time duration produced by an appropriate signal generator external to the test chamber 116. The frequency of the sinusoidal pulse is adjusted to match the resonance frequency of the transducer 111 and the time duration is adjusted to be sufficiently short that the frequency spectrum of the pulse is approximately equal to or exceeds the operating bandwidth of the transducer 111. With these adjustments of the excitation signal, the sound wave produced in the gas will have the minimum rise time and the fewest number of oscillatory cycles as governed by the bandwidth of the transducer 111. In this regard, the preferred embodiment of the speed of sound sensor 10 will utilize a transducer 111 having a maximum practical bandwidth in order to produce ultrasonic pulses having the shortest practical time duration. For this purpose, piezoceramic transducers designed specifically for efficient acoustical coupling into air or other gases are preferred which have a −6 dB bandwidth in the range of 75–100 percent of the transducer resonance frequency. However, ultrasonic transducers having a −6 dB bandwidth of 40–50 percent of the resonance frequency may be used in sensor 10 to yield satisfactory speed of sound measurements under many operating conditions and accuracy requirements.

The distance, d, separating reflecting surfaces 113 and 114 is adjusted to provide a sound propagation time delay between the two reflected ultrasonic pulses sufficient to prevent the pulses from overlapping in time. For example, to ensure good time separation between the two reflected pulses, the time delay, $\Delta t$, should be about ten times greater than the duration of the pulse. Thus, for an ultrasonic pulse having a frequency f, and a time duration, $\delta$, containing N cycles, i.e., $\delta = N/f$, the distance, d, is, from Equation (2) above, $$d = \frac{v_{gas} \Delta t}{2} = \frac{v_{gas}}{2}\left(\frac{10N}{f}\right) = 5N\lambda \quad (3)$$

Where $$\lambda = \frac{v_{gas}}{f} = \text{wavelength}$$

of the sine wave comprising the pulse signal in the gas under test. As one specific example, if N=3 cycles and the transducer resonance frequency is 500 kHz and the speed of sound in the gas is 1450 ft/sec, the separation distance, d, should be d=5(3)(1450(12)/(500,000)=0.522 in.

Referring again to FIG. 3, two sequential reflected ultrasonic pulses detected by the transducer 111 are illustrated. Also shown in FIG. 3 are time windows, defined by times $t_{11}$ to $t_{12}$ and $t_{21}$ to $t_{22}$, adjusted to bracket the first and second reflection pulses as a preparatory step in separating the pulses for time delay analysis.

Figure 4:
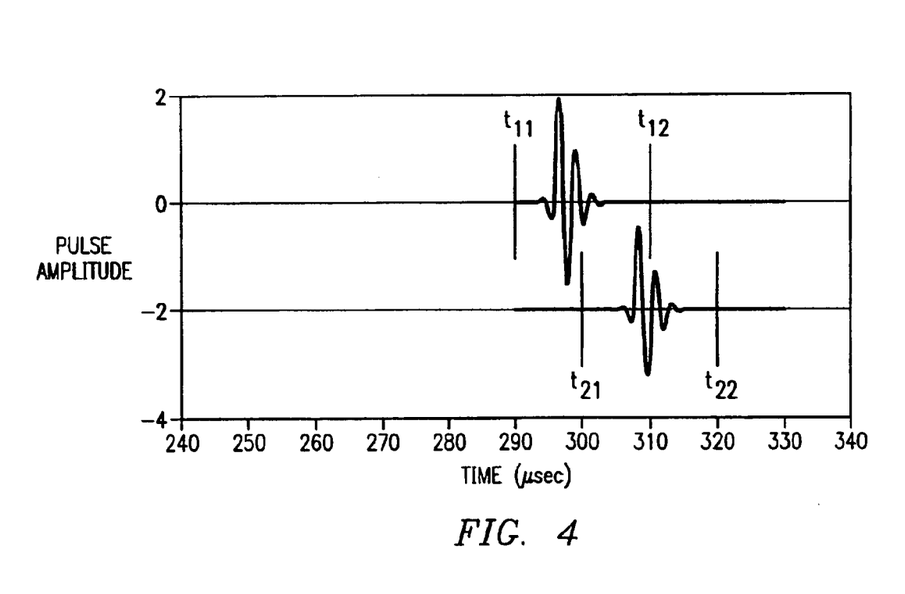
FIG. 4 shows the two reflected pulses separated and having a specified time delay shift preparatory to signal processing.
Figure 5:
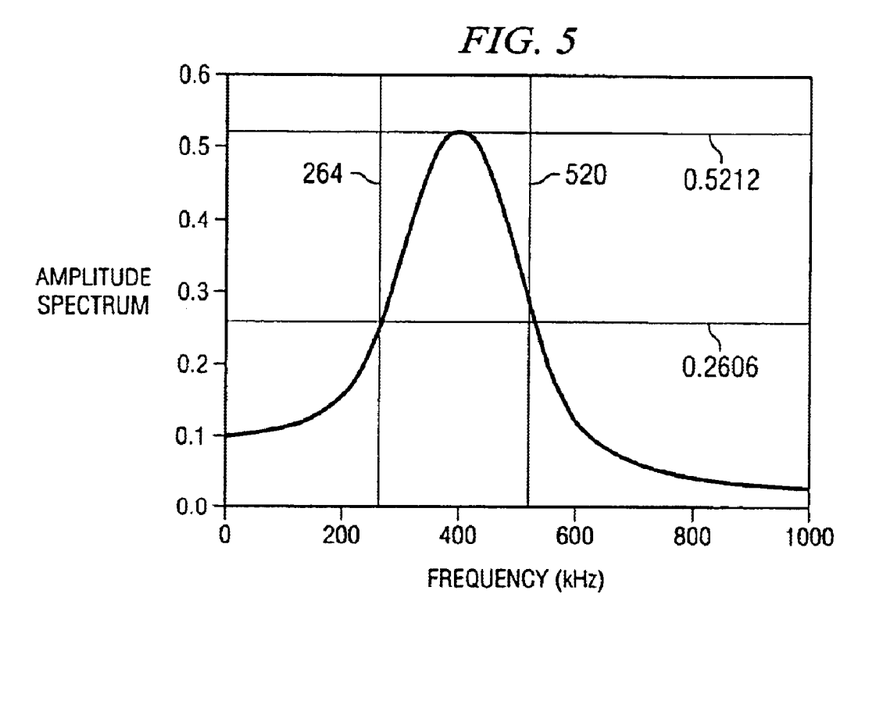
FIG. 5 illustrates the frequency spectrum of the detected ultrasonic pulses.

FIG. 4 shows the two reflected pulse signals after separation by selecting them in their respective time windows shown in FIG. 3 to form two time-series pulse waveforms. FIG. 4 also shows the earlier arriving pulse to be shifted in time toward the later arriving pulse by a selected precisely known time delay which, as further described below, facilitates determining their separation in time. The received ultrasonic pulse waveforms are digitally sampled at very short time intervals to provide a very high time resolution of the waveforms. To derive the time delay between the pulses from these signals, they are processed by cross correlation whereby the first signal is incrementally time shifted and multiplied by the second signal and the product averaged to yield an analytical measure of the coherence or similarity of the two pulses. The cross correlation process is expressed mathematically by $$R_{12}(\tau_m) = \frac{1}{N}\sum_{n=0}^{N} P_1(t_n - \tau_m)P_2(t_n) \qquad (4)$$

where: $P_1(t)$=discrete-time-sampled pulse signal 1;
$P_2(t)$=discrete-time-sampled pulse signal 2;
$\Delta t_{sample}$=digital sampling time interval;
$\tau_m = m\Delta t_{sample}$=correlation time lag;
$0 \leq m \leq M = (t_{22} - t_{11})/\Delta t_{sample}$; and
$N = t_{22}/\Delta t_{sample}$ FIG. 5 illustrates the relatively wide bandwidth of the frequency spectra of the reflected pulses. This relatively wide bandwidth is inherently associated with the relatively short time duration of the ultrasonic pulses and is an important characteristic of the invention for accurately determining the time delay between the two pulses.

Figure 6:
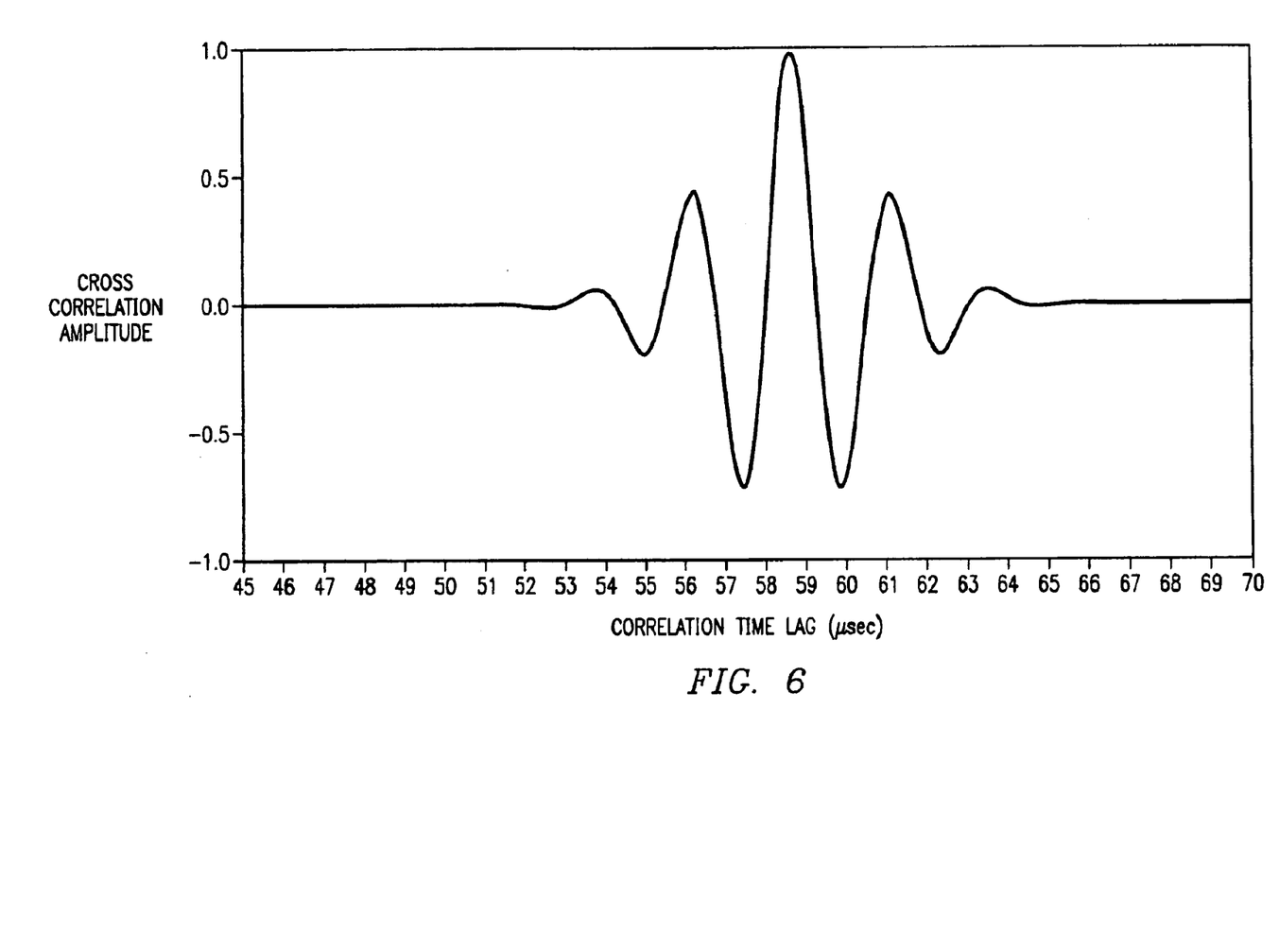
FIG. 6 illustrates the results of cross correlating the reflected pulses of FIG. 3.

FIG. 6 shows a plot of the cross correlation function, $R_{12}(\tau_m)$, calculated for two reflected pulse signals having approximately three oscillation cycles each. The cross correlation function, $R_{12}(\tau)$, has a positive maximum value at a value, $\tau = \tau_{max}$, representing the number of lag steps, $m = m_{peak}$, at which the peak value of $R_{12}(\tau_{max})$, occurs. This time lag corresponds to the time delay, $\Delta t$, between the two reflected ultrasonic pulses and may be resolved to within the nearest time lag interval, $\Delta\tau_{max} = m_{peak}\Delta t_{sample}$. Thus, the digital sampling rate used in recording the reflected ultrasonic signals governs the time resolution to which the travel time delay, $\Delta t$, may be determined.

Speed of Sound Sensor with Helical Channel

Figure 7:
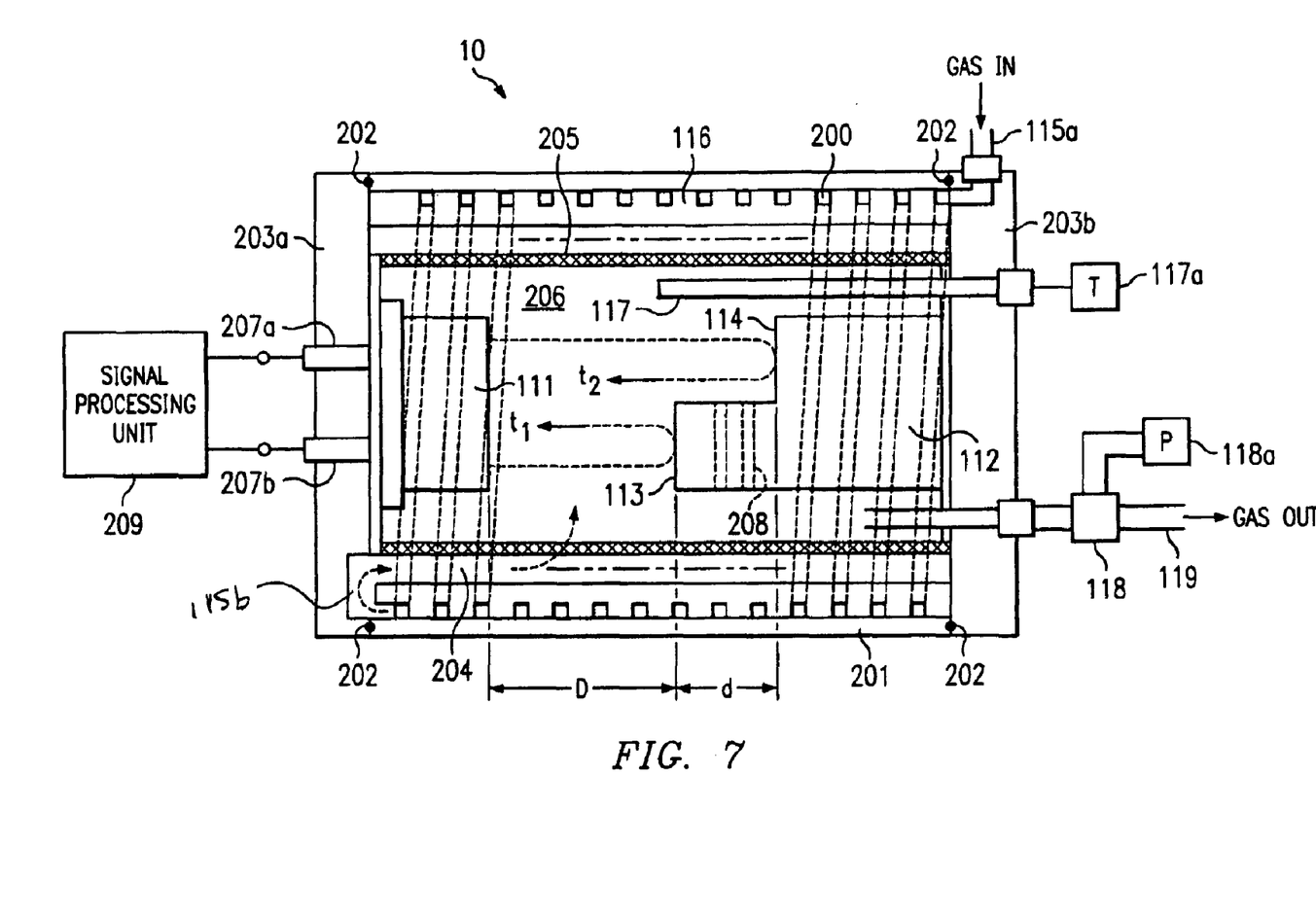
FIG. 7 shows a detailed embodiment of the speed of sound sensor using the two-reflector technique.
Figure 8:
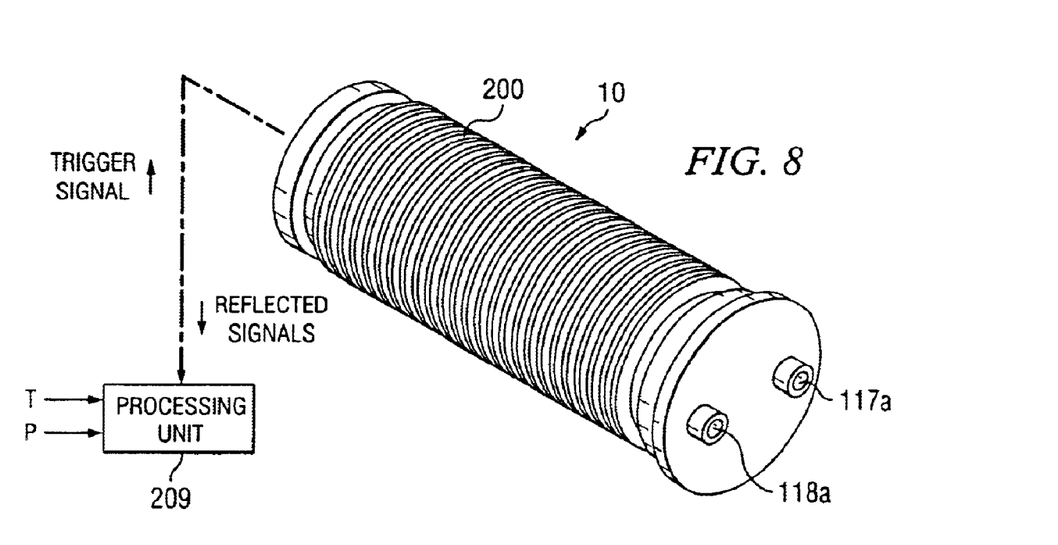
FIG. 8 is a perspective view of the speed of sound sensor.

FIG. 7 illustrates a more complete drawing of the speed of sound sensor 10 in accordance with the invention. This drawing shows the principal components of sensor 10 described above comprising the test chamber 116, the ultrasonic transmit-receive transducer 111, and the two-reflector target block 112 with reflecting surfaces 113 and 114. FIG. 7 also shows a specific means by which the temperature of the gas to be tested is equilibrated to the temperature of the test chamber 116 prior to entering the speed of sound measurement zone within the chamber 116. FIG. 8 is a perspective view of sensor 10, without an outer housing, illustrating flow channel 200.

A basic principle of operation of sensor 10 is that the thermal mass of the test chamber 116 is used as a heat sink to bring the test gas to the same temperature as chamber 116. This is accomplished on a continuous basis as the gas flows through sensor 10.

More specifically, as shown in FIG. 7, a helical flow channel 200 is arranged around the circumference and along the length of sensor 10. For example, one specific method by which the helical flow channel 200 may be intimately associated with the test chamber 116 is to construct it in the form of a groove, somewhat similar to a screw thread, machined into the outer surface of the cylindrical test chamber 116. This groove is then closed by a close-fitting outer sleeve 201 to form the helical flow channel 200. The outer sleeve 201 is sealed at the chamber end plates 203a and 203b by O-rings 202 so that the entire internal volume of sensor 10, including the helical flow channel 200, will retain the gas pressure. One end plate 203b is arranged to accept gas flowing into inlet 115a and, through an internal path, directs it into the upstream end of the helical flow channel 200. The gas then flows through the helical flow channel 200 and will travel a substantial distance around the chamber 116 until it reaches the opposite end 115b of the flow channel 200 at end plate 203a. The flow rate of the gas is adjusted to a value such that all parcels of gas within the flow channel 200 make moving contact with the sides of the flow channel 200 and, hence, contacts the chamber 116 for a substantial time period. During this time period, the gas will give up or accept heat energy from the chamber 116 so as to equilibrate to the same temperature of the chamber 116 by the time it exits the flow channel 200 at end plate 203a.

An internal path in end plate 203a directs the equilibrated gas into an annular space 204 where it travels freely between the inner wall of the chamber 116 and a porous cylindrical metallic sleeve 205, concentric with chamber 116, through which it diffuses into the speed of sound measurement volume 206 in the inner part of the chamber 116. By traveling through the helical flow channel 200 and diffusing uniformly through the porous metal sleeve 205, the gas is assured to have the same temperature as the chamber 116. The gas throughout the measurement volume 206 will have uniform temperature.

The use of the porous sleeve 205 minimizes possible streaming flow in the gas transport motions and serves as a final point of intimate contact with the gas for thermal equalization. Sleeve 205 makes the flow more uniform by reducing jetting at the end of the helical flow channel 115b. Another important function of porous sleeve 205 is to provide anechoic conditions within the speed of sound measurement volume 206 in the inner part of chamber 116 by reducing reflections of any ultrasonic waves that contact the sleeve 205. If desired, sleeve 205 may be made from a material that is rough surfaced as well as porous. Essentially, diffuser sleeve 205 serves the function of scattering and absorbing any ultrasonic pulse signals that reverberate within the chamber 116, thereby improving the signal-to-noise ratio of signals received by transducer 111.

Ultrasonic transducer 111 is located in the inner space 206 of chamber 116 at one end of chamber 116. It emits the short duration sound wave pulse whose time of travel between reflecting surfaces 113 and 114 is measured.

An electrical excitation voltage pulse, more specifically a repetitive sequence of triggered pulses having the form of a gated sine wave, is applied to transducer 111. The frequency of the sine wave corresponds to the resonance frequency of the transducer 111. The repetition rate of the transmitted pulses is not critical to the speed of sound measurements. However, this repetition rate is selected so that any possible reverberation within the chamber 116 dies away between successive pulses and, if necessary, is also selected to be sufficiently low that the average power delivered to transducer 111 does not exceed the power rating of transducer 111.

Each applied voltage pulse actuates transducer 111, resulting in an emitted ultrasonic pulse. The ultrasonic pulse travels through the test gas to the opposite end of chamber 116 where it is reflected from surfaces 113 and 114 on target block 112. As explained, below, transducer 111 is a broad bandwidth transducer.

Electrical connections to transducer 111 are brought out of chamber 116 at end plate 203a by means of feedthrough terminals 207a and 207b to maintain the pressure integrity of the chamber 116.

FIG. 7 further illustrates the dual-face structure of target block 112. Target block 112 is of one-piece construction, and is made from a material having a low coefficient of thermal expansion.

Two specific examples of suitable materials for target 112 are Invar® and Super Invar®. Invar® and Super Invar® have thermal expansion coefficients of 1.5E-06 in/in/F and 0.35E-06 in/in/F, respectively. Super Invar® is a well-known steel alloy that exhibits a nearly zero coefficient of thermal expansion. This alloy consists of steel with 32% nickel, 5.5% cobalt, and smaller amounts of other elements for machinability. In reference to target 112, an important concern is dimensional stability when exposed to temperature variations, thus a good choice is Super Invar®.

A suitable construction of target block 112 is two semicircular faces 113 and 114 of a cylinder such that the semicircular faces are oriented parallel to the face of transducer 111. By using the one-piece two-reflector rigid metal target block 112, the derived speed of sound is independent of uncertainties in the effective distance between the local mechanical-acoustical coupling interface between the transducer 111 and the test gas as well as the reflecting surfaces on the target block 112. When made of a low thermal expansion material, the spacing between faces 113 and 114 is essentially independent of temperature and, therefore, the time delay between the pulses reflected at faces 113 and 114 is also essentially independent of temperature.

Gas outlet port 119 is in fluid communication with pressure sensor 118 and 118a and permits the pressure within chamber 116 to be determined. Gas outlet port 119 also permits the gas to exit sensor 10. Small gas flow channels 208 are located in target block 112 to allow the gas near the reflecting surface 114 to more easily move toward outlet port 119.

As an example, the distance, D, between the transducer and the near reflecting surface 113 is approximately 2 inches. A typical distance, d, between the two reflecting surfaces 113 and 114 is 0.500 inch. A typical length dimension of transducer 111 is approximately 1.5 inch. A typical length of target block 112 is 2 inches. Given these dimensions, the remainder of test chamber 116 dimensions would be sized appropriately, resulting in a total length of sensor 10 of approximately 6.5 to 7 inches. A typical diameter of transducer 111 is 1.25 inch and a typical inside diameter of porous sleeve 205 is 1.75 inch. Given these dimensions, the remainder of the chamber 116 diameter, including the helical flow channel 200 groove and the outer sleeve 201 would be sized appropriately, resulting in a total diameter of sensor 10 of approximately 2.5 inches. More specifically, the helical flow channel 200 in chamber 116 may typically have a rectangular cross-section approximately 0.09-inch deep and 0.06-inch wide and a groove-to-groove pitch of 0.125 inch. These dimensions combined with a typical outside diameter of the chamber body 116 of 2.25 inch will result in a total helical flow channel length of approximately 300 inches. At a gas flow rate of 0.2 liter/minute, the dwell time of the gas in this helical flow channel 200 is approximately 8.6 seconds.

Sensor Data Processing Correlation Methods

The above-described speed of sound sensor is an example of a "two-reflector" speed of sound sensor, that is, a speed of sound sensor that employs ultrasonic pulse-echo reflections from two target faces separated by a known distance. The experimental parameter derived from this sensing technique is the difference in the two-way travel time between the two detected reflections. This time difference is derived by numerically computing the cross correlation between the two reflections to obtain a statistically precise measure of their time separation. The current version of this speed of sound sensor is capable of providing direct measurements of sound speed in natural gas mixtures with an accuracy and resolution of approximately 0.46 ft/sec when operating at gas pressures of 60 psia or higher and when the ultrasonic pulse waveforms are digitally sampled at 50 MSamples/sec and the nitrogen concentration is provided by separate means. This accuracy corresponds to a measurement precision of about 320 parts per million for typical natural gas mixtures (sound speed: 1,400±100 ft/sec) present in transmission pipeline environments. To satisfy the speed of sound sensing accuracy required by the two-state inferential algorithm, with its ability to eliminate the need for separate information on nitrogen concentration, this present sound speed accuracy and resolution must be improved by a factor of five.

Extending the present sound speed resolution by a factor of five could be achieved by directly digitizing the reflected sound pulse waveforms at 250 MSamples/sec. However, such high-speed analog-to-digital conversion is impractical for use in robust and cost-effective commercial equipment. A more practical approach is one in which the current 50 MSamples/sec ultrasonic reflection waveforms are transferred from the sensor electronics system to a data processing module for supplemental analysis to numerically interpolate the desired precision speed of sound measurements. This approach utilizes the proven parts of the present speed of sound sensor and allows the ultrasonic waveform analysis to be performed in a high-level computational code that can provide powerful signal processing for reflection waveform cross correlation analysis, interpolation of precision values of travel time differences between the two reflections, and calculation of the desired engineering values of measured speed of sound.

The pulse reflections from the target surfaces 113 and 114 return to transducer 111 where, by reciprocal transducer action, they are detected and recorded in digital form. A signal processing unit 209 accepts the digitized pulse waveforms and performs appropriate calculations to determine the difference in travel time, Δt, between the reflected ultrasonic pulses using the cross correlation method described above in association with Equation (4). Processing unit 209 also receives and records signals representing temperature and pressure from sensor transmitters 117a and 118a.

The distance, d, between the two reflecting faces of target block 112 is very stable with temperature. The speed of sound is derived from the measured time difference, Δt, between the two detected pulse reflections by the relation involving distance, d, as given by Equation (2) above.

The detected sound wave pulses are digitally sampled and recorded with sufficient time resolution that their times or arrival at the transducer 111 may be measured to within a typical time resolution of about $1/f_s=0.02$ μsec ($f_s$=50 MSample/sec) in order to accommodate the numerical interpolation process mentioned above and, hence, achieve the desired accuracy in the derived speed of sound. For example, to initially achieve a speed of sound measured to an accuracy of $\Delta v_{gas}=\pm 0.1$ percent, or less, in a methane-dominated natural gas mixture, the digital sampling rate of the ultrasonic pulse waveforms may be expressed approximately as:

$$f_{sample} \approx \frac{v_{gas}^2}{2d\Delta v_{gas}} \quad (5)$$

For a gas having a speed of sound of $v_{gas}$=1,420 feet/second and a desired measurement precision of 0.50 foot/second, if d=0.500 inch, the digital sampling rate of the received ultrasonic pulse waveform must be, by Equation (5), $f_{sample}$= 48.4×10$^6$ samples/second. The digitally sampled sound pulses are then subjected to correlation analysis to derive their relative time delay to within $\Delta\tau_{max}$=0.02 μsec and the resulting cross correlation function is further subjected to an interpolation process, described in detail below, to significantly improve the time resolution of the cross correlation coherence peak value time of occurrence.

For most natural gas mixtures, ultrasonic transducers having an operating resonance frequency in the range of 300–500 kHz and a bandwidth of 75–100 percent of the operating resonance frequency are capable of providing ultrasonic pulse-echo signals having acceptable signal-to-noise ratio when using two-way reflection path lengths of about 6 inches, or less. Likewise, ultrasonic pulses in the 300–500 kHz frequency range are capable of providing the desired speed of sound accuracy stated in the above example when their waveforms are sampled and digitized at a sampling rate of 48×10$^6$ samples/second. Frequencies and bandwidths outside this range may also be suitable.

Transducer 111 in FIG. 7 is capable of operating with a preferred resonance frequency in the range of 300–500 kHz. Furthermore, transducer 111 has a preferred relatively wide bandwidth in the range of 75–100 percent of its resonance frequency. As described above, such a wide bandwidth characteristic is required for generating short time duration ultrasonic pulses that, in turn, yield a well-defined cross correlation function peak by which the time delay between the reflected pulses is determined.

Figure 9A:
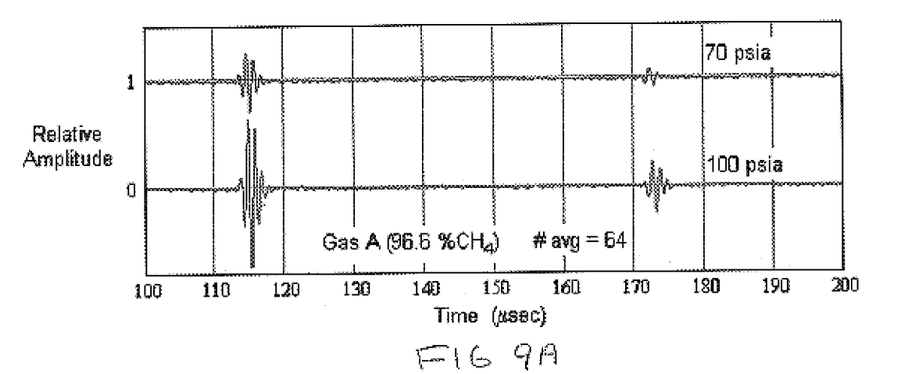
FIGS. 9A–9C are examples of pulse-echo waveforms.
Figure 9B:
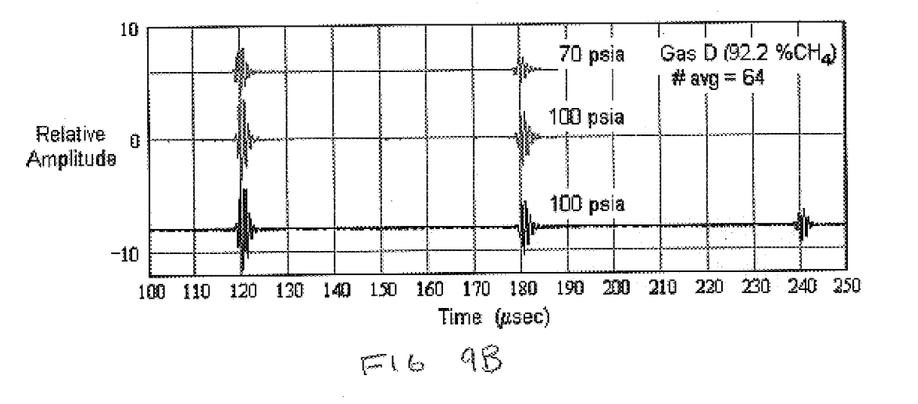
Figure 9C:
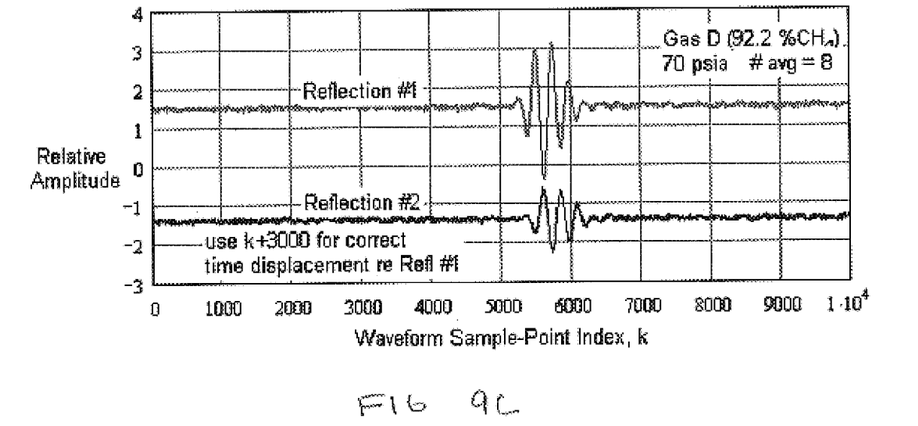

FIGS. 9A–9C illustrate discrete-time signals each containing an early-time reflection wavelet and a later-time reflection wavelet. These waveforms represent the analog ultrasonic signals at the output of the receiver after conversion to 12-bit digital form at a sampling rate of 50 Msamples/sec and stored in 10,000-word trace files.

The traces in FIGS. 9A and 9B show the complete waveform containing the two reflection wavelets separated by a time difference of approximately $\Delta T \cong 60$ μsec. The traces in FIG. 9A are low in amplitude because of inefficient acoustical coupling into the low-density test gas and, by comparing the amplitudes of the first and second reflections, also indicate that this gas attenuates the sound waves by a factor of about 1/3.5 over the separation distance of 2·d=1 inch. Signal averaging of 64 waveforms was used in this example to improve the signal-to-noise ratio of the second reflection. The higher gas density at 100 psia pressure improves the acoustic coupling and the observed signal strength as shown in the lower trace of FIG. 9A. The traces shown in FIG. 9B were recorded in a test gas having a somewhat higher density and lower absorptive attenuation than that used for the traces shown in FIG. 9A. Signal averaging of 64 traces is adequate to provide good signal-to-noise ratios in this test gas. The lower trace in FIG. 9B shows the arrival of a secondary reflection at a time equal to twice that of the first reflection, indicating that it is the first multiple reflection between the transducer 111 and the first reflector face 113.

The traces in FIG. 9C are separate shorter-time-base recordings of the first and second reflections to illustrate their wavelet details and typical noise contamination. The second reflection has lower amplitude than the first reflection because of absorptive attenuation effects in the gas. The natural gas composition used in these tests exhibits relatively high attenuation, resulting in the second reflection being reduced by a factor of about 1/2.1. Somewhat higher attenuation and associated weaker ultrasonic signals can be expected in gas compositions containing higher methane content. Natural gas compositions having methane content up to 98 mol % are occasionally encountered in commercial natural gas transmission and distribution systems.

The physical path length, 2·d, between the two reflection faces is known and invariant. Hence, the travel time difference, ΔT, between the two reflections is a measure of the speed of sound in the gas at the measured pressure and temperature conditions in the test chamber 116.

As discussed above, a "two state" method acquires measurements at two different thermophysical states (State 1 and State 2). Because the speed of sound in the gas at State 1 conditions is different from the speed of sound at State 2 conditions, the time difference between the reflection wavelets are also different. For typical natural gas compositions at testing pressures of P1=70 psia and P2=150 psia over a wide range of energy meter ambient temperatures and for a known target separation distance 2·d=1 inch, the two-way reflection time differences will be bounded in the range of approximately 55 μsec<ΔT<65 μsec. Thus, the cross correlation function between the first and second reflection wavelets may be obtained by computing the "autocorrelation" function of the waveform, using a correlation lag-time window defined by 0≤τ≤65 μseconds, where τ is the correlation time-lag parameter.

A reasonably accurate value of the first reflection arrival time, t1, which, by the design of the gas test chamber, is in the range 100 μsec<$t_1$<140 μsec, may be found by sorting out the maximum positive sample value of the waveform in the t1 time window and identifying its sample-time index, k1. The approximate time of arrival of the maximum positive waveform peak in the first reflection is then given by:

$$t_1 = \frac{k_1}{f_s} \quad (6)$$

where $f_s$ is the analog-to-digital ultrasonic signal sampling rate (50 MSamples/sec).

The sorting process referred to above may be replaced by a threshold amplitude detection process without significant loss of accuracy in the identified value of t1 for the purpose of defining the required waveform trace length and the correlation lag-time window bounds. For example, if the value, k1=6,110, were found from a given recorded waveform, the value of t1 would be:

$$t_1 = \frac{6110}{50 \times 10^6} = 122.2 \ \mu sec \quad (7)$$

and the arrival time, t2, of the second reflection in the recorded waveform would be in the range:

$$t_1+55 \ \mu sec=177.2 \ \mu sec<t_2<t_1+65 \ \mu sec=187.2 \ \mu sec \quad (8)$$

which, when expressed in terms of the sample-point index, k, corresponds to the sample-point range of 8860<k<9360.

Cross correlation computation is accomplished using the discrete-time function $$R_p = C \cdot \sum_{k=K1}^{K2} w_k \cdot w_{k-p} \tag{9}$$

$$C = \frac{1}{R_{p\max}} \tag{10}$$

where $R_p$ is a cross correlation function; p is a correlation lag window index; $w_k$ is a digitally sampled ultrasonic signal waveform; K1 and K2 are start and end bounds of selected waveform sample points used in the correlation calculation; and C is a normalizing coefficient derived from the computed correlation function by which the maximum value of Rp ($R_{p\max}$) in the correlation function is made unit amplitude.

In computing the cross correlation function, the product, $w_k \cdot w_{k-p}$, need not be calculated for the entire waveform file since the sample points in the waveform trace in advance of the first reflection contain no information relevant to the later arriving reflection wavelets and the sample points well after the second reflection contain only residual secondary reflections within the gas test chamber. Specifically, the ultrasonic signal receiver is designed to mute the incoming signal during the first 30–40 µsec to suppress electrical feedover from the excitation pulse applied to the ultrasonic transducer and secondary reflections begin at a time equal to twice the first reflection, i.e., at 2t1. Therefore, the active elements in the waveform file may be specified to begin at a sample point $w_{K1}$ somewhat earlier than the first reflection time and end at sample point wK1 slightly less than 2t1. That is, for example, by arbitrary choice, select:

$$K1 = t_1 - \Delta T$$

$$K2 = t_1 + 0.8 \cdot t_1 = 1.8 \cdot t_1 \tag{11}$$

In reference to Equation (9), if the indicated calculation begins at time-lag p=0, the correlation function $R_p$ includes the autocorrelation function of the entire waveform trace. This calculated autocorrelation part of $R_p$ contains no useable information regarding the time difference between the two reflection wavelets. Thus, in order to avoid the autocorrelation result and other unnecessary early lag-time calculations, the correlation lag-time index may start at an index point, p=P1, specified to be somewhat earlier than the first reflection time, t1. To reliably compute the cross correlation function between the first and second reflections in all anticipated gas mixtures and pressure-temperature conditions, the lag-time index must extend to p=P2 where P2 corresponds to a time somewhat greater than the upper sample-point upper bound given in Equation (11). This lag-time shift range, P1<p<P2, may be specified to eliminate the unnecessary correlation responses and minimize the computation time required to yield the cross correlation function.

Figure 10:
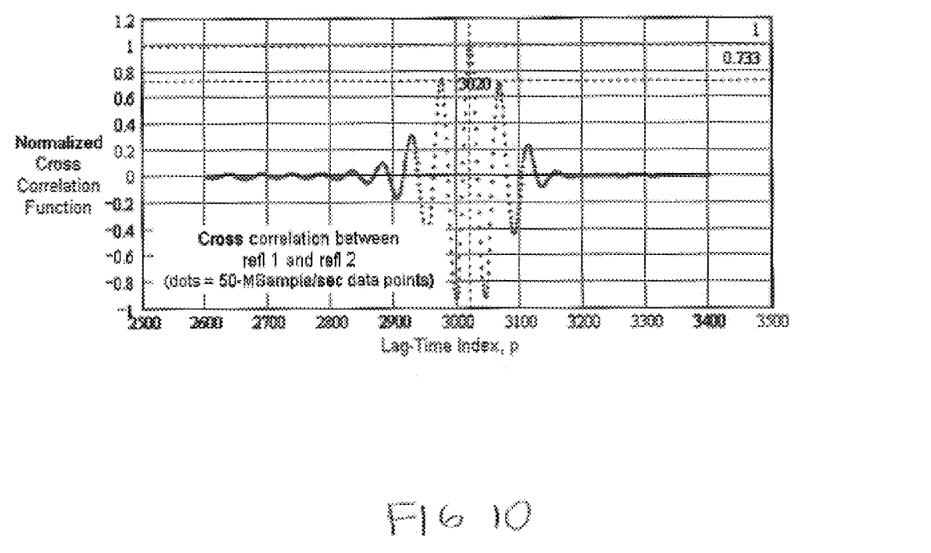
FIG. 10 illustrates the cross-correlation between Reflection 1 and Reflection 2 of FIG. 9B.

FIG. 10 illustrates the cross correlation function derived from the truncated waveform illustrated in the lower trace shown in FIG. 9B, using an 800-point time-lag window ranging from sample-points p=6000 to p=6800. The lag-time shift at the sample point closest to the coherence maximum, i.e., $p_{max}$=3019, is:

$$\Delta T = \frac{p_{\max}}{f_s} = 60.40 \ \mu\text{sec} \tag{12}$$

The corresponding speed of sound is, for 2·d=1 inch, $$v_{gasD} = \frac{2\Delta R \cdot \left(\frac{1}{12}\right)}{\Delta T} = 1379.691 \ \text{ft/sec} \tag{13}$$

Values of $p_{max} \pm 1$ lead to the resolution limit imposed by the 50-MSample/sec signal sampling rate (±0.457 ft/sec). A more accurate coherence maximum point exists between lag-time points $p_{max} \pm 1$. This maximum coherence point may be found by curve-fit interpolation applied to the positive coherence lobe of the correlation function.

The computational procedure described above is a direct, time-domain implementation of the autocorrelation function in which the correlation lag time exceeds the time delay between the first and second reflections. This procedure is preferred when the correlation analysis is implemented in a microprocessor operating under firmware program execution. This time-domain procedure has the advantage that the resulting reflection wavelet coherence lag time for the two reflections is a direct indication of the reflection time delay, ΔT, required in the speed of sound calculation. The computation time of this procedure may be reduced by introducing supplemental steps of gating each reflection in an accurately defined time window and computing the cross correlation function using only the sample points in the time windows. The total time lag corresponding to ΔT is then calculated as the sum of lag time derived from the windowed reflection signals and the time separation between the two time windows. This procedure eliminates a relatively large number of correlation calculations at sample points between the sample windows but requires an accurate record of the time window end points. For the ultrasonic reflection wavelet durations shown in FIG. 9A, the computation time can be reduced to about one-half that required by the autocorrelation computing technique described earlier.

When the cross correlation analysis is implemented in a compiled software code, the preferred computing procedure is one involving the Fourier transforms of the time windowed reflection wavelets. This procedure is based on the duality between the convolution process in the time domain and the cross spectral energy density in the frequency domain. This process involves computing the Fourier transforms of the two windowed reflection signals, multiplying one transform by the complex conjugate of the other transform to obtain the cross spectral density, and computing the inverse transform to obtain the cross correlation function in the time domain. This time domain result will indicate the wavelet coherence time lag associated with the windowed reflections. The total time lag corresponding to ΔT is then calculated as the sum of lag time derived from the windowed reflection signals and the time separation between the two time windows. The width of the two time windows should be approximately 1,000 sample points to fully contain the reflection wavelets and also provide a buffer time range to allow wavelet overlap and cross-over sufficient to calculate the central lobes of the cross correlation function, including the central positive coherence lobe. By adjusting the two time windows to exactly $2^{10}$=1,024 sample points, the Fast Fourier Transform algorithm may be employed in the software code for very efficient computations.

For the exemplary speed of sound sensor and ultrasonic transducer, the coherence maximum of the cross correlation function shown in FIG. 10 is about 35 percent higher in amplitude than its adjacent positive sub-maxima. This difference is inherently related to the bandwidth and, correspondingly, to the number of oscillation cycles in the ultrasonic pulses. Therefore, as long as the ultrasonic waveforms are invariant in wave shape, i.e., approximately constant in frequency spectrum, the 35-percent difference in amplitude may be relied upon as an amplitude threshold difference by which the positive coherence lobe and its maximum sample value may be found. Alternatively, the maximum value in $R_p$ may be found by using a numerical sorting process. By either method, the value, $R_{pmax}$, required in Equation (10) may be identified and used to normalize the cross correlation function to unit amplitude. The positive coherence lobe is accurately defined by selecting about 10 sample points on each side of the maximum sample point.

Correlation Coherence Lag Time Interpolation

A statistically determined interpolation of the time shift corresponding to the coherence maximum in FIG. 10 is obtained by fitting a second-degree polynomial, i.e., a parabola, to the sample points comprising the positive lobe of the cross correlation function.

Figure 11:
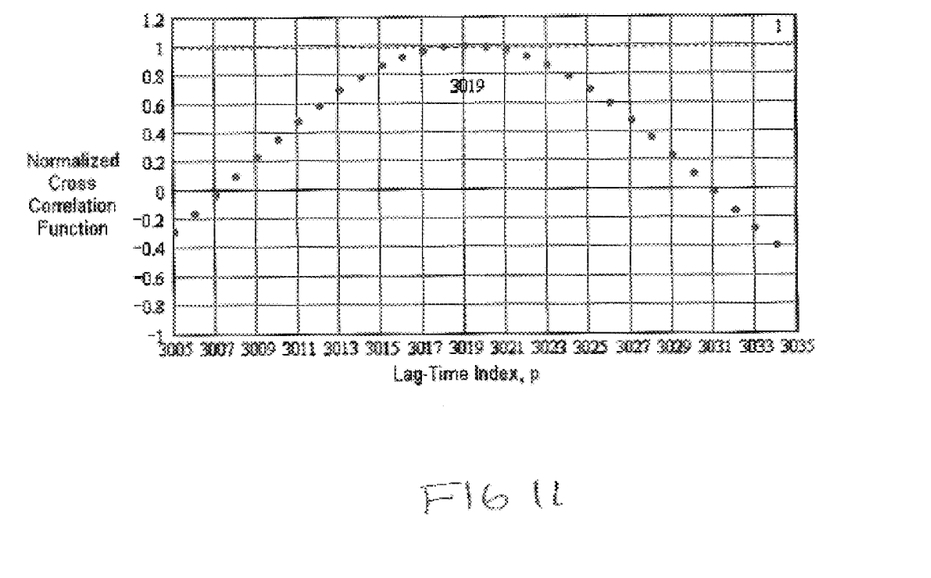
FIG. 11 is an expanded view of the positive lobe of the normalized cross correlation function of FIG. 10.

FIG. 11 shows an expanded view of the positive lobe in which there are 23 positive valued sample points (possibly up to 24 non-zero positive points in other examples). The cross correlation function is symmetrical about the coherence maximum and, although it has an exact analytical expression involving trigonometric functions related to the sound wave wavelet frequency and bandwidth, its isolated positive coherence lobe can be represented with good accuracy by a generalized parabola on the form:

$$f(\tau) = a_1 + a_2\tau + a_3\tau^2 \qquad (14)$$

Alternatively, using the relation, $\tau = p/f_s$, this function may be expressed in terms of the time-lag index, p, as:

$$f(p) = a_1 + a_2 p + a_3 p^2 \qquad (15)$$

This second degree polynomial is amenable to accurate curve fitting using the method of least squares, implemented using the least squares normal equations. With this direct arithmetical method, the residuals between the points on an optimally fitted analytical curve and the corresponding points to which it is fitted are minimized, resulting in a unique "most probable" fit to the data. In the present application, the symmetry of the correlation function about the true coherence maximum point ensures that the $\tau$- or p-axis coordinate of the vertex of the fitted parabola will accurately coincide with the coherence maximum lag-time coordinate (correlation lobe vertex) even though the maxima at the vertex points may not be equal.

The normal equations required to solve for the parabola coefficients, $a_1$, $a_2$, $a_3$ are $$A_1 a_1 + B_1 a_2 + C_1 a_3 = D_1$$
$$A_2 a_1 + B_2 a_2 + C_2 a_3 = D_2$$
$$A_3 a_1 + B_3 a_2 + C_3 a_3 = D_3 \qquad (16)$$

where j corresponds to p, J1 ... J2 is the range of points used in the data fitting process, and $$A_1 = J2 - J1 + 1 \quad B_1 = \sum_{j=J1}^{J2} j \quad C_1 = \sum_{j=J1}^{J2} j^2 \quad D_1 = \sum_{j=J1}^{J2} f(j) \qquad (17)$$

$$A_2 = B_1 \qquad B_2 = C_1 \quad C_2 = \sum_{j=J1}^{J2} j^3 \quad D_2 = \sum_{j=J1}^{J2} f(j) \cdot j$$

$$A_3 = C_1 \qquad B_3 = C_2 \quad C_3 = \sum_{j=J1}^{J2} j^4 \quad D_3 = \sum_{j=J1}^{J2} f(j) \cdot j^2$$

The data points representing the cross correlation function are such that the normal equations will be subject to round-off errors. As noted above, the values of the abscissa are large (p~3000) and appear in factors raised to the fourth power whereas values of the ordinate are less than unity and appear at only first power. This unbalance may be eliminated by shifting the cross correlation data points nearer to the abscissa origin to avoid numbers of large magnitude during the curve fitting calculations and then translating the result back to the original absissa position. That is, the positive data points of interest are identified and shifted to begin at the origin using a new index, j. The actual number of points, J1 ... J2, used in the curve fit is selectable to obtain the best fit (typically J2−J1+1 ≦17 for an accurate fit).

The normal equations may be solved by determinants to yield arithmetic expressions for the parabola coefficients as follows $$\Delta = A_1 B_2 C_3 + B_1 C_2 A_3 + C_1 B_3 A_2 - C_1 B_2 A_3 - B_1 A_2 C_3 - A_1 B_3 C_2 \qquad (18)$$

$$a_1 = \frac{1}{\Delta} \cdot (D_1 B_2 C_3 + B_1 C_2 D_3 + C_1 B_3 D_2 - C_1 B_2 D_3 - B_1 D_2 C_3 - D_1 B_3 C_2)$$

$$a2 = \frac{1}{\Delta} \cdot (A_1 D_2 C_3 + D_1 C_2 A_3 + C_1 D_3 A_2 - C_1 D_2 A_3 - D_1 A_2 C_3 - A_1 D_3 C_2)$$

$$a_3 = \frac{1}{\Delta} \cdot (A_1 B_2 D_3 + B_1 D_2 A_3 + D_1 B_3 A_2 - D_1 B_2 A_3 - B_1 A_2 D_3 - A_1 B_3 D_2)$$

Figure 12:
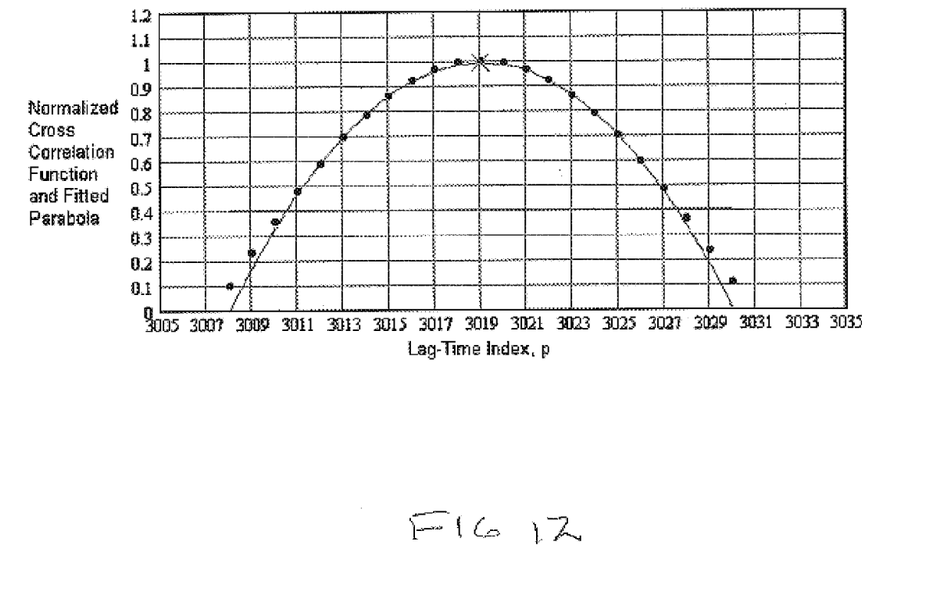
FIG. 12 illustrates the cross correlation function and least squares fitted interpolation parabola.

FIG. 12 shows the fitted parabola curve superimposed on the cross correlation sample points. This result illustrates the fitted curve after applying the least squares fit near the origin and shifting the resulting curve back to the correlation function range. The 17 points above the horizontal line represent the sample points in the range, J1 ... J2, used in the data coefficients.

In practice, points on the entire parabola curve are not required in order to derive the interpolated value of the vertex point. The exact vertex point of the parabola may be found by differentiating Equation (14) and solving for the abscissa corresponding to the maximum value. By this procedure, the exact vertex point, indicated by "X" in FIG. 12, has the coordinates $$p_{\max} = -\frac{a_2}{2 \cdot a_3} \quad f(p_{\max}) = a_1 - \frac{a_2^2}{4 \cdot a_3} \qquad (19)$$

-continued $$[p_{max}, f(p_{max})] = (3019.021, 0.994). \quad (20)$$

The interpolated speed of sound in the test gas is then found using only $p_{max}$ in the relation $$v_{gas} = \frac{2 \cdot d}{\left(\frac{p_{max}}{f_s}\right)} = \frac{\frac{1}{12} \cdot \text{ft}}{\frac{3019.021}{50 \times 10^6 \text{ samples/sec}}} = 1{,}380.138 \text{ ft/sec} \quad (21)$$

The value of $p_{max}=3019.021$ found in this example happens to be very close to an actual sample point on the cross correlation function, suggesting that interpolation was not necessary. However, in other test gases or at other pressure-temperature conditions, the interpolated value of pow could fall anywhere within the range $3018 < p_{max} < 3020$.

Speed of Sound Calibration Adjustment

There are several parameters in the speed of sound sensor system that may cause errors in the experimentally derived sound in the test gas. As noted from the expression for $v_{gas}$ in Equation (21), assuming that the true cross correlation coherence maximum is represented by the interpolated value, $p_{max}$, uncertainties in $f_s$ and d can independently introduce errors in the derived speed of sound. The sampling rate, $f_s$, set by a precision crystal oscillator in the sensor electronics system, may have a slight offset from 50 MSamples/sec and may also have a small frequency-drift temperature sensitivity. The exact value of d, although measurable with good precision, may also have a small temperature sensitivity caused by thermal expansion of the dual reflector target block. These temperature-related uncertainties are minimized in the present sensor system by using temperature stabilized electronic circuitry and by fabricating the reflector block from Super Invar® material having a near-zero thermal expansion coefficient. Residual temperature and offset uncertainties in $f_s$ and d are merged in their product, $f_s \cdot d$, as indicated in Equation (21). Thus, since stored values of $f_s$ and d are used in computing the speed of sound, either one of these stored values may be adjusted to serve as a basis for speed of sound calibration.

Accurate values of sound speed in known natural gas mixtures at known pressure and temperature may be calculated using a thermodynamic equation of state such as that currently designated by the gas industry as AGA-10. The speed of sound sensor may, therefore, be calibrated by temporarily introducing a certified natural gas mixture into the test chamber and experimentally deriving its speed of sound, $v_{gasREF}$, at accurately measured values of pressure and temperature using the reference value of $d_{ref}=0.5000$ inch stored in the data processing program. The true speed of sound in the certified mixture, $v_{gasCALC}$, is then calculated at the same pressure and temperature. The ratio of the calculated and reference sound speeds then serves as the calibration adjustment factor for the sensor derived speed of sound. That is, the calibrated speed of sound in an unknown test gas is then expressed by:

$$v_{gas} = \frac{2 \cdot d_{ref}}{\left(\frac{p_{max}}{f_s}\right)} \cdot \left(\frac{v_{gasCALC}}{v_{gasREF}}\right) \quad (22)$$

where $d_{ref}=0.5000$ inch, or other fixed reference value stored in the data processing program; $v_{gasREF}$=experimental speed of sound derived from sensor measurements using a certified natural gas mixture at measured pressure and temperature condition, and the stored value of $d_{ref}$; $v_{gasCALC}$=true speed of sound calculated using the AGA-10 equation of state for known natural gas mixtures at the same pressure and temperature condition used to determine the experimental reference value, $v_{gasREF}$.

Other Embodiments

Many variations and modifications may be made to the 20 disclosed embodiments of the invention without departing from the spirit and principles described herein. All such modifications and variations are intended to be included within the scope of the present invention, as defined by the following claims.

What is claimed is:

1. A method of processing reflection data acquired from a two-reflector sensor that measures the speed of sound in a gas, comprising the steps of:
    sampling two reflection signals acquired by the sensor, thereby obtaining two reflection data sets;
    computing the cross correlation between the two reflection data sets as a function of a lag time index, thereby obtaining a cross correlation function;
    fitting a second degree polynomial function to the positive lobe of the cross correlation function that contains the cross correlation coherence peak;
    computing the vertex of the polynomial function, thereby providing the time of occurance of the cross correlation coherence peak, which represents the travel time difference between the two reflections.

2. The method of claim 1, further comprising the step of digitally filtering the reflection data prior to the computing step.

3. The method of claim 1, wherein the digital filtering is implemented with median smoothing.

4. The method of claim 1, wherein the fitting step is performed at least squares calculations.

5. The method of claim 1, wherein the vertex is computed by differentiating the polynomial.

6. The method of claim 1, further comprising the step of calculating the speed of sound in the gas, using the travel time diference and the distance between the two reflectors.

7. The method of claim 6, wherein the speed of sound is calculated with a precision +/−0.1 percent.

8. The method of claim 1, wherein the sensor has an operating frequency in the range of 300–500 kHz.

9. The method of claim 1, wherein the sensor has a bandwidth in the range of 75–100 percent its operating frequency.

10. The method of claim 1, wherein the sampling rate is in the range of 48–50 samples per second.

11. The method of claim 1, wherein the lag time index is to a time-lag window beginning slightly earlier than the first reflection arrive time and slightly less than twice the first reflection arrival time.

12. A method of processing reflection data acquired from a two-reflector sensor that the speed of sound in gas, comprising:
    sampling two reflection signals acquired by the sensor, thereby obtaining two reflection data sets;
    computing the cross correlation between the two reflection data sets as a function of time, thereby obtaining a cross correlation function:
    fitting a parabolic function to the lobe of the cross correlation function that contains the cross correlation coherence maximum;

computing the vertex of the function, thereby providing the time of occurrence of the cross correlation coherence maximum, which represents the travel time difference between the two reflections.

13. The method of claim 12, wherein the function of time is a function of a time-lag index value, which is indexed to the lag time between the two signals.

14. The method of claim 12, wherein the fitting step is performed by least squares calculations.

15. The method of claim 12, wherein the vertex is computed by differentiating the polynomial.

16. The method of claim 12, further comprising the step of calculating the speed of sound in the gas, using the travel time difference and the distance between the two reflectors.

17. The method of claim 16, wherein the speed of sound is calculatred with a precision +/−0.1 percent.

18. The method of claim 12, wherein the sensor has an opportunity frequency in the range of 300–500 kHz.

19. The method of claim 12, wherein the sensor has a bandswidth in the range of 75–100 percent of its operating frequency.

20. The method of claim 12, wherein the sampling rate is in the range of 48–50 samples per second.

21. The method of claim 12, wherein the lag time index is to a time-bag window beginning slightly earlier than the first reflection arrival time and slightly less than twice the first reflection arrival time.

22. An improved speed dual-reflection type sensor for measuring the speed of sound in gas, the sensor having a processin device programmed to perform the following steps:
   sampling two reflectioin signal acquired by the sensor, thereby obtaining two reflection data sets;
   computing the cross correlation between the two reflection data sets as a function of time, therby obtaining a cross correlation function;
   fitting a parabolic function to the lobe of the cross correlation function that contains the vertex of the function, therby providing the time of occurrene of the cross correlation coherence maximum, which reprents the travel time difference between the two reflections.

23. The sensor of claim 22, wherein the processing device is programmed with firmware.

24. The sensor of claim 22, wherein the processing device is programmed with software.

25. A method of processing reflection data acquired from a two reflection sensor that measures the speed of sound in gas, comprising;
   at first temperature/pressure state of the gas:
   sampling two reflection signals acquired by the sensor, thereby obtainig two
   reflection data sets;
   computing the cross correlation between the two reflection data sets at a
   function of time, thereby obtaining a cross correlation function;
   fitting a parabolic function to the lobe of the cross correlation function that contains the cross correlation coherence maximum;
   computing the vertex of the function, thereby providing the time of occurrence of the cross correlation coherence maximum, which represents a first travel time differnce between the two reflections;
   at a second temperature/pressure state of the gas, repeating the above steps, thereby obtaining a second travel time differenc;
   using the first and second travel time differences to calculate a first speed of sound value and a second speed of sound value;
   calculating at least one property of the gas using the first and the second speed of sound values.

26. The method of claim 25, wherein the step of calculating a property of the gas is performend by calculating the heating value of the gas.

27. The method of claim 25, wherein the step of calculating a property of the gas is performed by calculating the nitrogen concentration of the gas.

* * * * *

UNITED STATES PATENT AND TRADEMARK OFFICE
CERTIFICATE OF CORRECTION

| | |
|---|---|
| PATENT NO. | : 7,107,851 B2 |
| APPLICATION NO. | : 10/894084 |
| DATED | : September 19, 2006 |
| INVENTOR(S) | : Thomas E. Owen |

Page 1 of 1

It is certified that error appears in the above-identified patent and that said Letters Patent is hereby corrected as shown below:

Title page, [73]. Please insert --Gas Research Institute, Des Plaines, IL-- as co-assignee.

Signed and Sealed this

Nineteenth Day of August, 2008

JON W. DUDAS
*Director of the United States Patent and Trademark Office*